(12) United States Patent
Zhu et al.

(10) Patent No.: US 10,362,968 B2
(45) Date of Patent: Jul. 30, 2019

(54) BIOIMPEDANCE CIRCUMFERENCE MEASUREMENT

(71) Applicant: FRESENIUS MEDICAL CARE HOLDINGS, INC., Waltham, MA (US)

(72) Inventors: Fansan Zhu, Flushing, NY (US); Nathan W. Levin, New York, NY (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 0 days.

(21) Appl. No.: 14/772,884

(22) PCT Filed: Apr. 17, 2013

(86) PCT No.: PCT/US2013/036921
§ 371 (c)(1),
(2) Date: Sep. 4, 2015

(87) PCT Pub. No.: WO2014/137363
PCT Pub. Date: Sep. 12, 2014

(65) Prior Publication Data
US 2016/0007884 A1  Jan. 14, 2016
US 2019/0183385 A9  Jun. 20, 2019

Related U.S. Application Data

(63) Continuation-in-part of application No. PCT/US2011/055916, filed on Oct. 12, 2011, and a
(Continued)

(51) Int. Cl.
*A61B 5/107* (2006.01)
*A61B 5/053* (2006.01)
*A61B 5/00* (2006.01)

(52) U.S. Cl.
CPC ............ *A61B 5/1072* (2013.01); *A61B 5/053* (2013.01); *A61B 5/0537* (2013.01);
(Continued)

(58) Field of Classification Search
CPC .............. A61B 19/46; A61B 2019/461; A61B 2019/463; A61B 5/0537; A61B 5/4869;
(Continued)

(56) References Cited

U.S. PATENT DOCUMENTS 3,536,258 A  10/1970  Rocheleau
3,832,780 A * 9/1974  Lewis ...................... A41H 1/02
33/15
(Continued)

FOREIGN PATENT DOCUMENTS

GB  2452256 A * 3/2009 ............ A61B 5/107
JP  2004512128     4/2004
(Continued)

OTHER PUBLICATIONS

International Search Report from PCT/US2013/036921, dated May 22, 2014.
(Continued)

*Primary Examiner* — Adam J Eiseman

(57) ABSTRACT

Apparatus is disclosed for measuring the circumference of a limb of an individual, e.g., the individual's arm and/or calf. The apparatus uses one or more magnetic strips which surround the limb and contain magnetic coding of length information. Tension is applied to the magnetic strip by a tensioning assembly, which can be a pressure cuff or a stepping motor, and a magnetic read head reads the magnetic coding of length information from the strip. When used in a bioimpedance analysis procedure, the length information can be used to convert measured voltage differences into normalized bioimpedance values, e.g., resistivity values.

19 Claims, 6 Drawing Sheets

Related U.S. Application Data continuation-in-part of application No. 13/879,220, filed as application No. PCT/US2011/055916 on Oct. 12, 2011.

(60) Provisional application No. 61/774,891, filed on Mar. 8, 2013, provisional application No. 61/393,544, filed on Oct. 15, 2010.

(52) U.S. Cl.
CPC .......... *A61B 5/4875* (2013.01); *A61B 5/6824* (2013.01); *A61B 5/6828* (2013.01); *A61B 5/6831* (2013.01); *A61B 5/6838* (2013.01); *A61B 2560/0425* (2013.01); *A61B 2562/0209* (2013.01)

(58) Field of Classification Search
CPC ... A61B 5/4872; A61B 5/4875; A61B 5/4878; A61B 5/4881; A61B 5/107; A61B 5/6831
USPC ........................................................ 600/587
See application file for complete search history.

(56) References Cited

U.S. PATENT DOCUMENTS

| | | | |
|---|---|---|---|
| 5,413,582 | A | 5/1995 | Eaton |
| 6,125,297 | A | 9/2000 | Siconolfi |
| 6,151,523 | A | 11/2000 | Rosell Ferrer et al. |
| 6,338,723 | B1 * | 1/2002 | Carpenter ............ A61F 13/069 602/60 |
| 6,532,384 | B1 | 3/2003 | Fukuda |
| 6,615,077 | B1 | 9/2003 | Zhu et al. |
| 7,072,710 | B2 | 7/2006 | Chamney |
| 7,133,716 | B2 | 11/2006 | Kraemer et al. |
| 7,228,170 | B2 | 6/2007 | Zhu et al. |
| 8,801,645 | B2 * | 8/2014 | Lipshaw ............... A61F 13/085 450/101 |
| 9,167,857 | B2 * | 10/2015 | Jang ........................ A41F 9/002 |
| 2005/0131310 | A1 * | 6/2005 | Freund ............... A61B 5/02233 600/499 |
| 2006/0122540 | A1 | 6/2006 | Zhu et al. |
| 2009/0062728 | A1 | 3/2009 | Woo |
| 2009/0062730 | A1 | 3/2009 | Woo |
| 2010/0198100 | A1 | 8/2010 | Oku et al. |
| 2010/0292619 | A1 * | 11/2010 | Redington ........... A61H 9/0078 601/84 |
| 2011/0009757 | A1 | 1/2011 | Sano et al. |
| 2012/0172747 | A1 | 7/2012 | Fukuda et al. |

FOREIGN PATENT DOCUMENTS

| | | |
|---|---|---|
| WO | 2004049938 | 6/2004 |
| WO | 2005027717 | 3/2005 |
| WO | 2006002656 | 1/2006 |
| WO | 2006042218 | 4/2006 |
| WO | 2012051261 A2 | 4/2012 |

OTHER PUBLICATIONS

International Preliminary Report on Patentability in PCT/US2013/036921, dated Sep. 17, 2015.
International Search Report and Written Opinion dated (May 2, 2012), for PCT/US11/55916 (11 pages).
Zhu et al., "Continuous Measurement of Calf Resistivity in Hemodialysis Patients uning Bioimpedance Analysis", (2006), pp. 5126-5128.
Zhu et al., "A method for the estimation of hydration state during hemodialysis using calf bioimpedance technique", 29, (2008), pp. S503-S516.
Supplementary Partial European Search Report dated (Oct. 4, 2017), for application No. (3 pages).
Moissl, et al. "Body fluid volume determination via body composition spectroscopy in health and disease." Physiological measurement 27.9 (2006).
Duggan, Time to abolish "gold standard" BMJ. Jun. 13, 1992; 304(6841): 1568-1569.
Versi, "Gold standard" is an appropriate term. BMJ. Jul. 18, 1992; 305(6846): 187.
Wystrychowski, et al. (2007). Dry weight: Sine qua non of adequate dialysis. Advances in Chronic Kidney Disease, 14 (3), Abstract.
Chamney et al., "A new technique for establishing dry weight in hemodialysis patients via whole body bioimpedance," Kidney Int., 2002, 61 :2250-2258.
Kuhlmann et al., Bioimpedance, Opinion in dry weight Nephrology and and blood Hypertension, pressure control: 2005, new 14:543-549.
Piccoli et al., "A new method for monitoring body fluid variation by bioimpedance analysis: The RXc graph," Kidney Int., 1994, 46:534-539.
Zhu et al., "Adjustment bioimpedance of dry of weight the in calf," Int J hemodialysis Artif Organs, patients 2004, using 27:104-109.
Zhu et al., "Prediction of Normal Hydration State in Hemodialysis Patients Using Calf Resistivity" [Abstract], J Am Soc Nephrol, 2010, 21:435A.
Chamney et al., "A whole-body model to distinguish excess fluid from the hydration of major body tissues," Am J Clin Nutr, 2007, 85:80-89.

* cited by examiner

BIOIMPEDANCE CIRCUMFERENCE MEASUREMENT

CROSS-REFERENCE TO RELATED CASES FOR U.S. NATIONAL PHASE APPLICATION

This application is a U.S. National Phase of International Patent Application No. PCT/US2013/036921, filed on Apr. 17, 2013, which is hereby incorporated herein by reference in its entirety. This application is also a continuation-in-part of co-pending International Application No. PCT/US2011/55916, filed Oct. 12, 2011, which claims the benefit under 35 U.S.C. § 119(e) of U.S. Provisional Application No. 61/393,544, filed Oct. 15, 2010. This application also claims the benefit under 35 U.S.C. § 119(e) of U.S. Provisional Application No. 61/774,891, filed Mar. 8, 2013. The contents of International Application No. PCT/US11/55916 and U.S. Provisional Applications Nos. 61/393,544 and 61/774,891 are hereby incorporated herein by reference in their entireties.

FIELD

This disclosure relates to methods and apparatus for measuring the circumference of a limb of an individual, e.g., an individual's calf. The measured circumference is used to determine a physiological property, e.g., the individual's hydration state, using a bioimpedance procedure. As one example, the methods and apparatus disclosed herein can be used in determining the degree of fluid overload in dialysis patients.

BACKGROUND

Bioelectrical impedance analysis (BIA) is a commonly-used, non-invasive technique for estimating the composition of the body of a human or animal. It has been practiced in whole body and segmental formats. In broad outline, current is applied to the body between at least two spatially-separated points (the current application points) and the voltage difference produced by the applied current is measured between at least two other spatially-separated points (the measurement points). Typically, the measurement points are located inboard of the current application points. Measurements can be performed at a single frequency or at a series of frequency, in which case the technique is sometimes referred to as BIA spectroscopy.

The impedance Z is determined by taking the ratio of the measured voltage V divided by the applied current I, where Z, V, and I are, in general, complex numbers. Although the impedance Z can be of value for some applications, normally, it is desirable to normalize the impedance (or one of its components) by the physical dimensions of the portion of the body over which the measurement was taken. For example, it is often desirable to derive a resistivity ($\rho$) value from a resistance (R) value using the equation $\rho = R \cdot A/L$, where L is length and A is cross-sectional area, e.g., $A = C^2/4\pi$ for a circular cross-section whose circumferential length is C.

Of the two dimensions L and A, L is normally easier to estimate. Thus, L can be well-approximated by the linear distance between the spatially-separated measurement points. Estimating A, on the other hand, is more difficult for the fundamental reason that body tissues are compressible.

Although health care and other professionals (e.g., weight loss coaches, physical trainers, and the like) can be taught to measure the circumference of a portion of the body with a tape measure, the measurement requires judgment as to how tight to make the tape. The need for judgment results in substantial and unacceptable variability between measurements made by different professionals, as well as in measurements made by the same professional with different individuals or the same individual on different occasions. For lay personal, the problem is markedly worse. Moreover, other than for measurements on the legs, circumference measurements are difficult for an individual to do on himself or herself, e.g., it is difficult to apply a tape measure to one's own arm. Even leg measurements can be difficult for some individuals whose eyesight and/or dexterity has been compromised.

The present disclosure addresses this problem of unreliable circumference measurement which has reduced the usefulness of BIA and, in particular, segmental BIA, both in clinical and at-home settings.

SUMMARY

Apparatus is disclosed for measuring the circumference of a limb of an individual which comprises:
  (a) one or more magnetic strips, each of which, during use of the apparatus, surrounds the limb and each of which, along its length, comprises magnetic coding of length information;
  (b) a magnetic read head for each magnetic strip for reading the magnetic coding of length information from the strip; and
  (c) a tensioning assembly for setting the tension of the one or more magnetic strips.

In accordance with an embodiment, apparatus is disclosed for measuring the circumference of a limb of an individual comprising a pressure cuff for application to the limb, said pressure cuff comprising;
  (a) one or more magnetic strips, each of which surrounds the limb when the pressure cuff is applied to the limb and each of which comprises magnetic coding along its length;
  (b) a magnetic read head for each magnetic strip for reading length information from the strip; and
  (c) a plurality of air stripes for setting the level of tension of the one or more magnetic strips.

In accordance with an embodiment, apparatus is disclosed for measuring the circumference of a limb of an individual comprising a housing for application to the limb, said housing being handle-shaped and housing:
  (a) one or more measuring tapes, each of which surrounds the limb when the handle-shaped housing is applied to the limb, each of which comprises a magnetic strip which has magnetic coding along its length;
  (b) a magnetic read head for each measuring tape for reading length information from the magnetic strip; and
  (c) for each measuring tape, a stepping motor for dispensing and applying tension to the measuring tape.

DESCRIPTION

Figure 1:
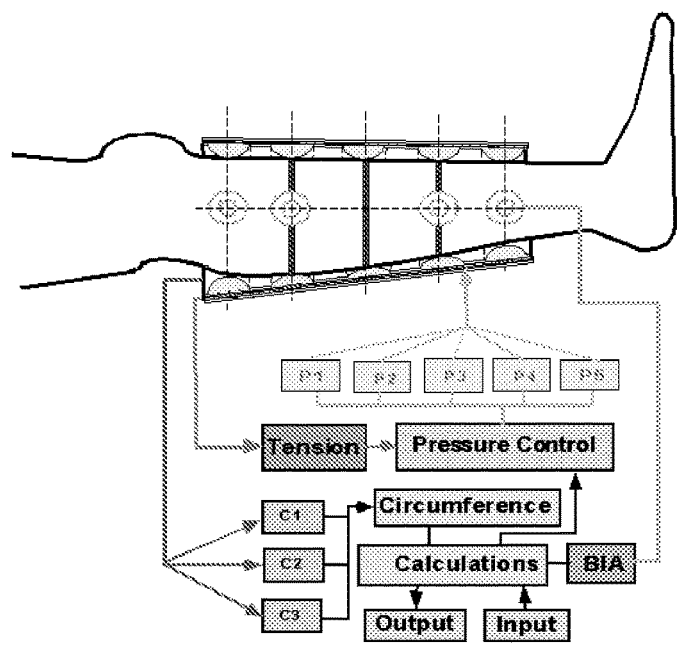
FIG. 1 is a schematic diagram of an exemplary embodiment of the present disclosure which employs a pressure cuff to apply current-injecting electrodes, measuring electrodes, and at least one magnetic strip to the limb of a subject in order to perform a bioimpedance procedure on the limb.
Figure 2:
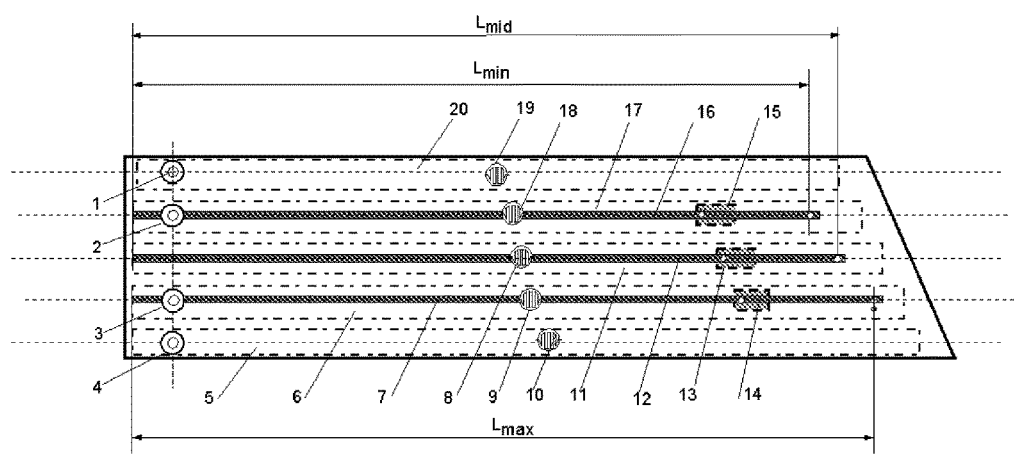
FIG. 2 is a schematic diagram showing the cuff of FIG. 1 in more detail.
Figure 3:
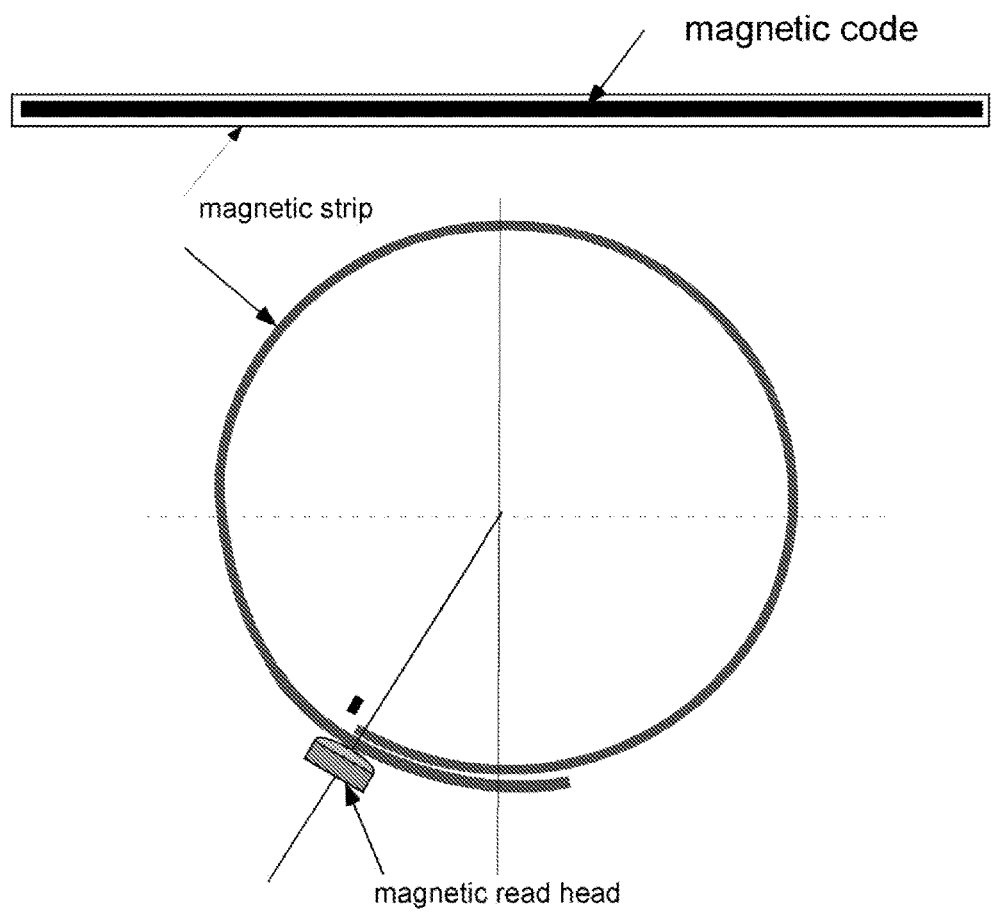
FIG. 3 is a schematic diagram illustrating one of the magnetic strips of the embodiment of FIGS. 1-2 and a magnetic read head for reading length information from the strip.

FIGS. 1-3 show an embodiment of an integrated calf bioimpedance monitor with circumference measurement. The apparatus uses one or more magnetic strips (see FIG. 3) integrated together with reusable or disposable electrodes into a pressure cuff with multiple, separate, air stripe areas for applying pressure to the electrodes and for setting the level of tension of the one or more magnetic strips during the circumference measurement (see FIGS. 1 and 2).

FIG. 1 shows the device on a user's calf, and FIG. 2 shows the cuff of FIG. 1 in more detail. Specifically, FIG. 2 shows the cuffs electrodes, tension sensors, air stripe areas and magnetic strips. In FIG. 2, the integrated electrodes are shown at 1-4, the tension sensors at 8, 9, 10, 18, and 19, the magnetic strips for obtaining circumference values at 7, 12, and 16, and the magnetic read heads for reading the magnetic strips at 13, 14, and 15.

Similar to a magnetic ID card, distance along the length of a magnetic strip can be scaled with, for example, 0.1 cm resolution by magnetic coding of the strip. The air stripe areas, e.g., the five areas as shown in FIG. 2, are inflatable separately with different pressures so as to control the tension of each air stripe area.

The circumference can be calculated according to the values read by the one or more magnetic read heads (see FIG. 3), e.g., three magnetic strips and three magnetic read heads at, for example, three different locations along the length of the user's calf, e.g., at locations which give maximum, middle, and minimum circumference measurements (see FIG. 1). Four electrodes, e.g., four reusable electrodes, are used, two for injecting current and two for measuring voltage, e.g., for measuring voltage between two measurement points 10 cm apart. The "input" and "output" components shown in FIG. 1 can, for example, be used to obtain data such as body height and weight. The results can be stored in the device and can also be sent to a remote location using a cable or by wireless communication.

Among other applications, the device of FIGS. 1-3 can be used for measuring body composition and fluid status for dialysis patients or any other patients who need to check hydration status or changes in body composition. The device can be used in a clinical setting or at home by a healthcare professional or by the person being measured by the device.

Among the advantages of devices of the type shown in FIGS. 1-3 are:

1) circumference can be measured for more than one cross-sectional area, e.g., three cross-sectional areas; 2) the interface between skin and electrodes can be kept constant by pressure control; 3) the tension sensors can be used to improve the accuracy of the circumference measurement by ensuring that a desired level of tension (e.g., 100-150 grams) is applied to the magnetic strips; 4) the multiple air stripe areas, e.g., the five air stripe areas shown in FIGS. 1 and 2, can be separately inflated with variable pressure to take account of the variety of geometric shapes of human and animal limbs, such as the calf; 5) the electrodes can be disposable or reusable; 6) the device can be used to measure any body segment; and 7) when used on the arm, the device can automatically produce values of, for example, standard blood pressure, degree of fluid status, muscle mass, and fat mass, with a single measurement protocol.

Figure 4:
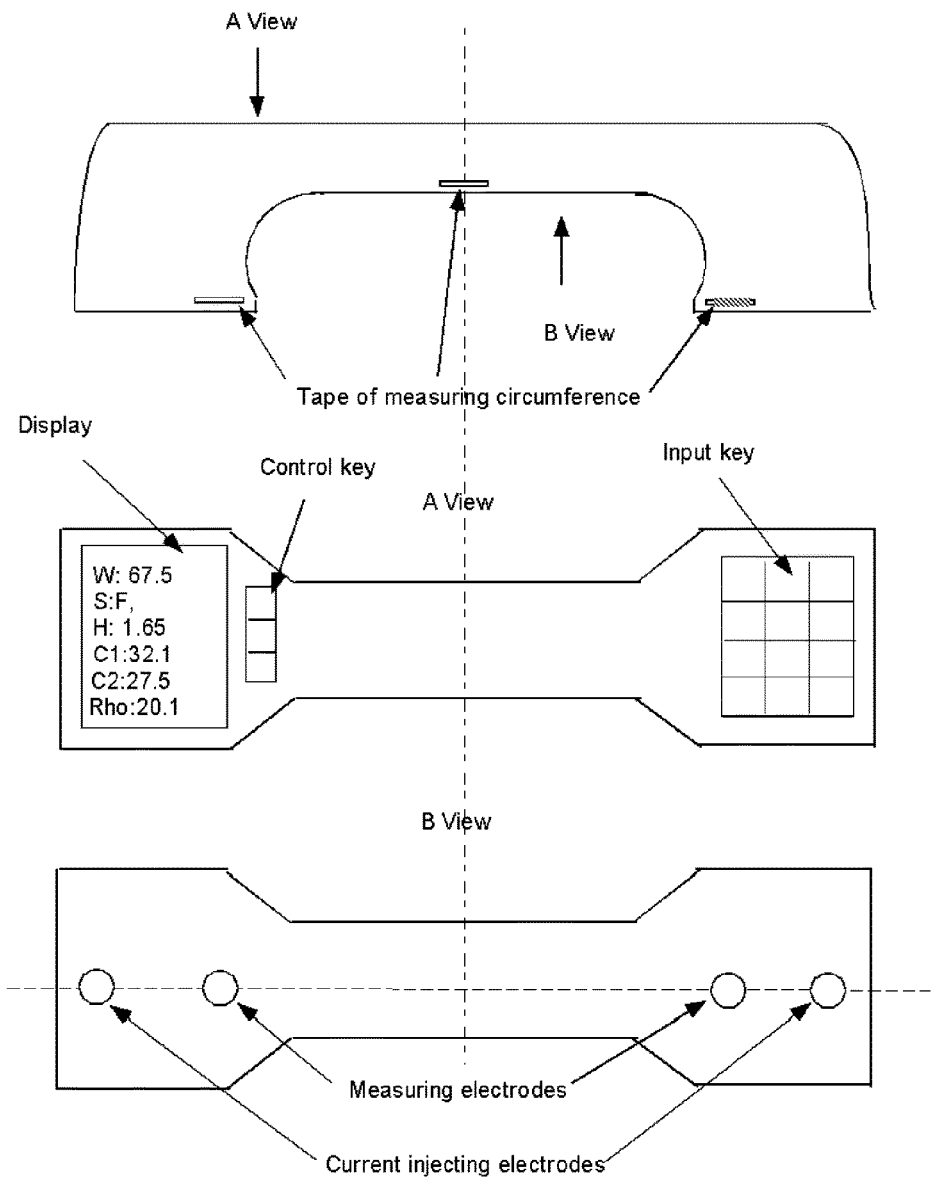
FIG. 4 is a schematic diagram of an exemplary embodiment of the present disclosure which employs a handle-shaped carrier to apply current-injecting electrodes, measuring electrodes, and at least one magnetic strip to the limb of a subject in order to perform a bioimpedance procedure on the limb.

FIGS. 4-7 show a further embodiment where the circumference measurement is performed using a handle-shaped device, rather than an inflatable cuff. The use of three circumference measuring tapes, i.e., three magnetic strips, is shown in FIG. 4, it being understood that more or less strips can be used as desired. The "A view" in FIG. 4, i.e., the middle panel, is a top view, and the "B view", i.e., the lowest panel, is a bottom view. The uppermost panel is a side view. By means of the device's handle configuration, during use, the bottom of the device (B view) can be easily pressed against the subject's skin, thus bringing the current injecting and measuring electrodes into firm contact with the limb whose properties are to be measured.

Figure 5:
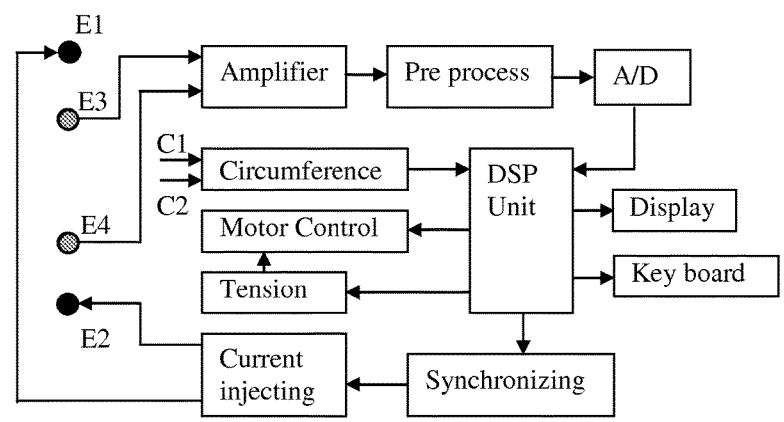
FIG. 5 is a block diagram of exemplary system components for use in the embodiment of FIG. 4.

The major components and functions of the device of this embodiment are illustrated in the block diagram of FIG. 5. Two electrodes (E1 and E2) are used to inject current, e.g., current at different frequencies in the range of, for example, 1 kHz to 300 kHz, and another two electrodes (E3 and E4) are used to measure the resulting voltage. In order to reduce noise, the signals can be pre-processed (e.g., with a pre-amplifier and a low pass filter) before being used to calculate an impedance, a resistance, and/or a reactance value between the measuring electrodes during the application of current between the injecting electrodes. An analog-to-digital converter (A/D converter) and a digital signal processing unit (DSP unit) are used to convert the measured analog signal to a digital signal and then to calculate impedance, resistance, and/or reactance at the different applied frequencies.

Parameters, such as, body weight, height and gender of the user (e.g., patient), can be inputted to the device using a small key board as shown in the middle panel of FIG. 4. A LCD display or other type of display can be used to display the inputted parameters and/or the results of the bioimpedance measurement and analysis, e.g., to display one or more circumference values, such as a maximum circumference value C1 and a minimum circumference value C2, and one or more bioimpedance values, such as, a ρ value. Other possible outputs include a hydration index, fat mass, muscle mass, ECV, ICV, and the like. The device can include a USB interface for downloading information from the device to a computer or communications device. As shown in FIG. 4, the device can include a control key for activating the bioimpedance measurement process.

Figures 6, 7:
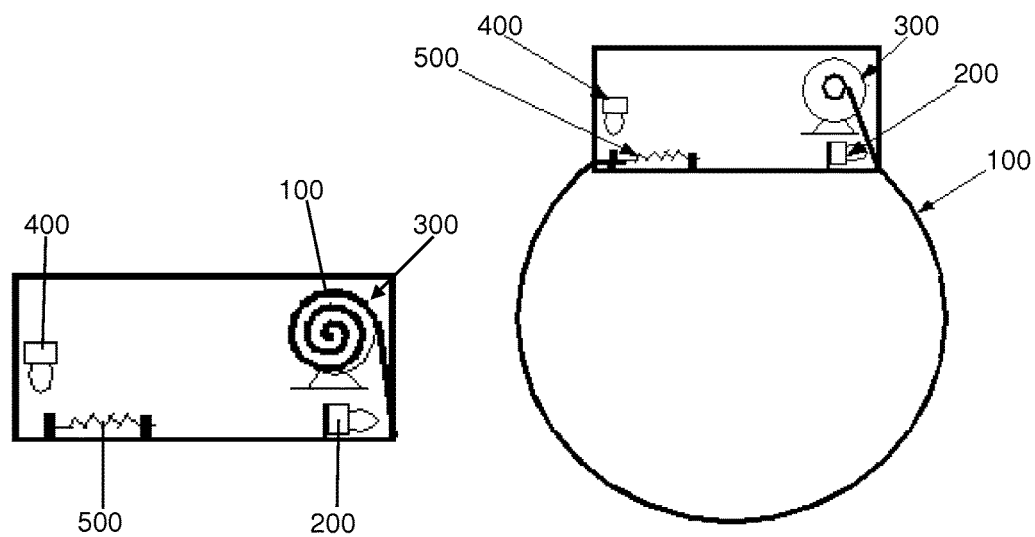
FIG. 6 is a schematic diagram showing an exemplary circumference measuring system for use in the embodiment of FIG. 4 prior to deployment of the system about a user's limb.
FIG. 7 is a schematic diagram showing the circumference measuring system of FIG. 6 after deployment about a user's limb (not shown in this figure).

FIGS. 6-7 show representative equipment for using a magnetic strip to measure the circumference of a user's limb. FIG. 6 shows a tape carrying the strip in its stored configuration, while FIG. 7 shows the tape deployed about the user's limb (not shown in FIG. 7). Specifically, 100 is the tape with the magnetic strip, 200 and 400 are magnetic read heads, 300 is a stepping motor for dispensing and applying tension to the tape, and 500 is a tension sensor.

Figure 10:
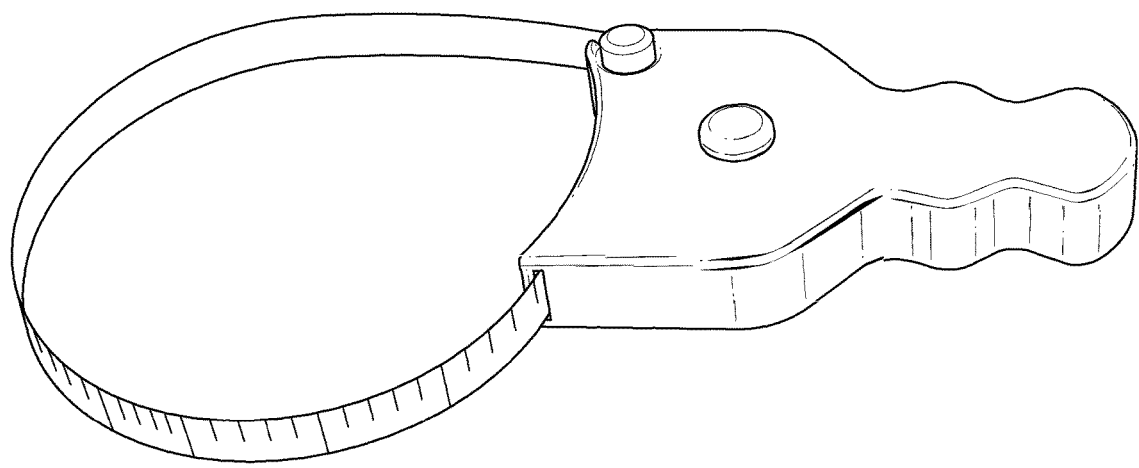
FIG. 10 is a photograph of the commercial circumference measuring device used in obtaining the vertical axis data of FIG. 8.

For the embodiment of FIGS. 4-7, a gap exists between the circumference measurement assembly and the user's skin, especially for the middle tape shown in the top panel of FIG. 4. Such a gap can also exist for the side tapes of FIG. 4, as well as for the embodiment of FIGS. 1-3, but usually will be of less concern. To address the potential effects of such a gap, a study was performed which compared manual calf measurements made by trained personnel using a conventional tape measure ($C_{Manual}$) with measurements made with a commercial diameter measuring device (see FIG. 10), where the user reads the length of the tape ($C_{Device}$) but the device determines the amount of tension applied to the tape.

Figure 8:
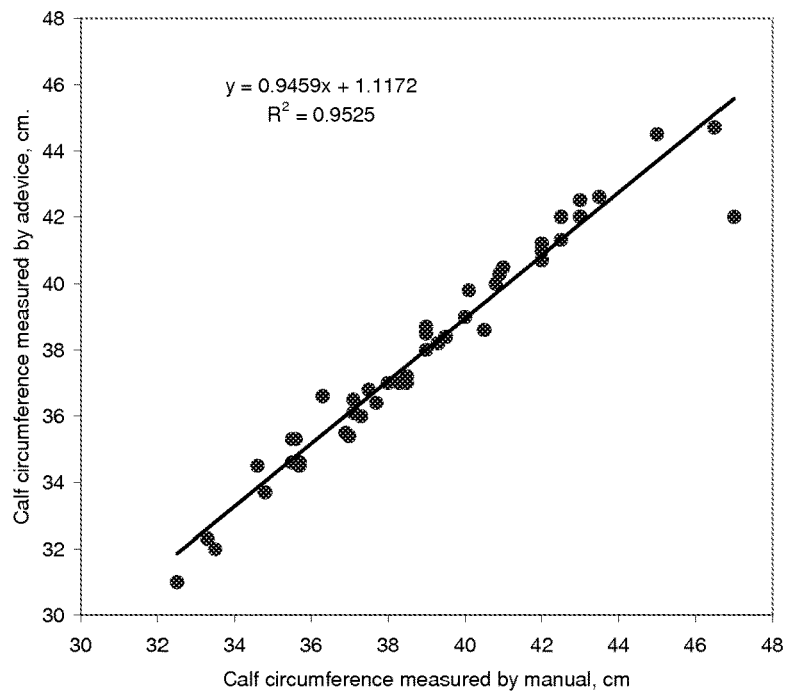
FIG. 8 is a graph comparing calf circumference measurements performed manually by trained individuals (horizontal axis) with calf circumference measurements performed using a commercial circumference measuring device (vertical axis).
Figure 9:
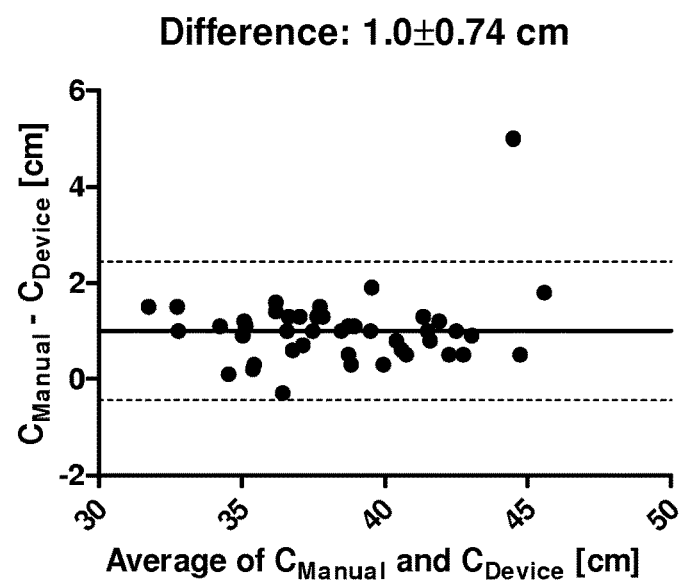
FIG. 9 is a Bland-Altman plot for the data of FIG. 8.

The results from 49 subjects are plotted in FIG. 8, where $C_{Manual}$ is plotted along the horizontal axis and $C_{Device}$ along the vertical axis. As can be seen in this figure, $C_{Device}$ is highly correlated with $C_{Manual}$ ($R^2=0.95$). The Bland-Altman analysis of FIG. 9 shows a difference (bias) between $C_{Manual}$ and $C_{Device}$ of 1.0±0.74 cm. This bias can be considered a systematic error that can be easily compensated for when circumference lengths are being used to convert measured voltages into normalized bioimpedance values, e.g., resistivity values. The data of this experiment thus shows that measurement of calf circumference using an automated device can provide accurate data to represent the actual value of a limb's circumference, e.g., a calf's circumference.

The apparatus and methods disclosed herein can be used in a variety of clinical applications, including without limitation: (1) measurement of hydration state (degree of hydration) for CKD, dialysis, peritoneal, or hemodialysis patients; (2) measurement of nutrition state for all patients through the provision of fat, muscle, cell mass, ECV, and/or ICV values for the leg or arm; and (3) detection of bleeding at any location of the body for surgical patients during recovery through the measurement of local changes in resistance.

It is to be understood that the foregoing summary and description of exemplary embodiments is intended to provide an overview or framework for understanding the nature and character of the invention. Additional features and advantages of the invention will be readily apparent to those skilled in the art from that description or recognized by practicing the invention as described herein. The accompanying drawings provide a further understanding of the invention, and are incorporated in and constitute a part of this specification. It is to be understood that the various features of the invention disclosed in this specification and in the drawings can be used in any and all combinations.

What is claimed is:

1. An apparatus for measuring the circumference of a limb of an individual comprising:
    two or more magnetic strips, each of which, during use of the apparatus, surrounds the limb and each of which, along its length, comprises magnetic coding of length information;
    a magnetic read head for each magnetic strip for reading the magnetic coding of length information from the strip;
    at least two current-injecting electrodes for injecting current at a plurality of frequencies, and at least two voltage-measuring electrodes for measuring resulting voltage between the at least two current-injecting electrodes;
    at least one of a pre-amplifier and a low pass filter for processing a signal received from the at least two voltage-measuring electrodes;
    an A/D converter for converting the signal from the at least one of the pre-amplifier and the low-pass filter;
    a digital signal processing unit for calculating at least one of impedance, resistance, and reactance at the plurality of the frequencies of injected current based on the converted signal received from the A/D converter, wherein the digital signal processing unit is configured to receive a single circumference measurement determined from a plurality of circumference measurements received from the magnetic strips;
    a tensioning assembly for setting the tension of the two or more magnetic strips; and
    a tension sensor for each magnetic strip;
    wherein the apparatus is configured to measure the circumference of the limb in a plurality of cross-sectional areas simultaneously for determining the plurality of circumference measurements.

2. The apparatus of claim 1 wherein the apparatus includes two current-injecting electrodes and two voltage-measuring electrodes.

3. The apparatus of claim 1 wherein the tensioning assembly includes a pressure cuff.

4. The apparatus of claim 3 wherein the pressure cuff includes a plurality of inflatable air stripes.

5. The apparatus of claim 4 wherein the inflatable air stripes are separately inflatable.

6. The apparatus of claim 3 wherein the pressure cuff includes two current-injecting electrodes and two voltage-measuring electrodes.

7. The apparatus of claim 1 wherein the apparatus includes a handle-shaped housing which has a middle portion and two side portions which extend away from the middle portion, each side portion having a bottom which contacts the limb during use of the apparatus.

8. The apparatus of claim 7 wherein a magnetic strip is housed in the middle portion of the handle-shaped housing.

9. The apparatus of claim 7 wherein a magnetic strip is housed in each of the side portions of the handle-shaped housing.

10. The apparatus of claim 7 wherein a magnetic strip is housed in the middle portion and each of the side portions of the handle-shaped housing.

11. The apparatus of claim 7 wherein the bottom of each side portion includes a current-injecting electrode and a voltage-measuring electrode.

12. The apparatus of claim 7 wherein the tensioning assembly includes a stepper motor.

13. A method of measuring the circumference of a limb comprising:
    applying an apparatus for measuring the circumference of the limb to the limb, the apparatus comprising:
        two or more magnetic strips, each of which, during use of the apparatus, surrounds the limb and each of which, along its length, comprises magnetic coding of length information;
        a magnetic read head for each magnetic strip for reading the magnetic coding of length information from the strip;

at least two current-injecting electrodes for injecting current at a plurality of frequencies, and at least two voltage-measuring electrodes for measuring resulting voltage between the at least two current-injecting electrodes;

at least one of a pre-amplifier and a low pass filter for processing a signal received from the at least two voltage-measuring electrodes;

an A/D converter for converting the signal from the at least one of the pre-amplifier and the low-pass filter;

a digital signal processing unit for calculating at least one of impedance, resistance, and reactance at the plurality of the frequencies of injected current based on the converted signal received from the A/D converter, wherein the digital signal processing unit is configured to receive a single circumference measurement determined from a plurality of circumference measurements received from the two or more magnetic strips; and a tensioning assembly for setting the tension of the two or more magnetic strips;

wherein the apparatus is configured to measure the circumference of the limb in a plurality of cross-sectional areas simultaneously for determining the plurality of circumference measurements;

activating the tensioning assembly; and reading length information from the magnetic strips.

14. The method of claim 13 wherein the limb is an arm.

15. The method of claim 13 wherein the limb is a calf.

16. A method of performing a bioimpedance analysis comprising:

applying an apparatus for measuring a circumference of a limb to the limb, the apparatus comprising:

two or more magnetic strips, each of which, during use of the apparatus, surrounds the limb and each of which, along its length, comprises magnetic coding of length information;

a magnetic read head for each magnetic strip for reading the magnetic coding of length information from the strip;

at least two current-injecting electrodes for injecting current at a plurality of frequencies, and at least two voltage-measuring electrodes for measuring resulting voltage between the at least two current-injecting electrodes;

at least one of a pre-amplifier and a low pass filter for processing a signal received from the at least two voltage-measuring electrodes;

an A/D converter for converting the signal from the at least one of the pre-amplifier and the low-pass filter;

a digital signal processing unit for calculating at least one of impedance, resistance, and reactance at the plurality of the frequencies of injected current based on the converted signal received from the A/D converter, wherein the digital signal processing unit is configured to receive a single circumference measurement determined from a plurality of circumference measurements received from the two or more magnetic strips; and a tensioning assembly for setting the tension of the two or more magnetic strips, wherein the apparatus is configured to measure the circumference of the limb in a plurality of cross-sectional areas simultaneously for determining the plurality of circumference measurements;

activating the tensioning assembly;

reading length information from the magnetic strips;

applying current to the limb using the current-injecting electrodes; and measuring a voltage difference between the voltage-measuring electrodes.

17. The method of claim 16 further comprising:

using the length information from the magnetic strips to convert a measured voltage difference into a normalized bioimpedance value.

18. The method of claim 17 wherein the normalized bioimpedance value is a resistivity value.

19. The method of claim 16 wherein the limb is a calf.

* * * * *